United States Patent
Higenbottam et al.

(10) Patent No.: US 6,739,332 B1
(45) Date of Patent: May 25, 2004

(54) INHALERS

(75) Inventors: Timothy William Higenbottam, Sheffield (GB); Benjamin Wolf Heller, Sheffield (GB); Keith Muir McCormack, Sheffield (GB)

(73) Assignee: The University of Sheffield, Sheffield (GB)

( * ) Notice: Subject to any disclaimer, the term of this patent is extended or adjusted under 35 U.S.C. 154(b) by 0 days.

(21) Appl. No.: 09/743,213

(22) PCT Filed: Jul. 7, 1998

(86) PCT No.: PCT/GB98/01994
§ 371 (c)(1),
(2), (4) Date: Oct. 3, 2001

(87) PCT Pub. No.: WO00/01434
PCT Pub. Date: Jan. 13, 2000

(51) Int. Cl.[7] .............................................. A61M 15/00
(52) U.S. Cl. .............................. 128/200.13; 128/203.12
(58) Field of Search ...................... 128/200.11, 200.12, 128/200.13, 200.14, 200.18, 200.21, 200.23, 203.12, 203.15, 203.16, 203.17, 203.19, 203.24, 204.14, 204.21, 204.23, 204.26

(56) References Cited

U.S. PATENT DOCUMENTS

| | | | | |
|---|---|---|---|---|
| 4,257,415 A | * | 3/1981 | Rubin | 128/200.21 |
| 4,945,929 A | * | 8/1990 | Egilmex | 131/273 |
| 5,299,565 A | * | 4/1994 | Brown | 128/200.21 |
| 5,404,871 A | * | 4/1995 | Goodman et al. | 128/200.14 |
| 5,474,059 A | * | 12/1995 | Cooper | 128/200.22 |
| 5,479,920 A | * | 1/1996 | Piper et al. | 128/204.23 |
| 5,813,397 A | * | 9/1998 | Goodman et al. | 128/200.14 |
| 6,000,394 A | * | 12/1999 | Blaha-Schnabel et al. | 128/200.19 |
| 6,158,431 A | * | 12/2000 | Poole | 128/203.12 |
| 6,192,876 B1 | * | 2/2001 | Denyer et al. | 128/205.25 |
| 6,237,589 B1 | * | 5/2001 | Denyer et al. | 128/200.21 |
| 6,260,549 B1 | * | 7/2001 | Sosiak | 128/200.23 |

* cited by examiner

Primary Examiner—Weilun Lo
Assistant Examiner—Teena Mitchell
(74) Attorney, Agent, or Firm—Synnestvedt & Lechner LLP

(57) ABSTRACT

There are many lung diseases and conditions for which the preferred form of treatment involves delivering a medicament of the appropriate sort down the Patient's airways into the lungs themselves. The most effective treatments involve the inhalation as an aerosol of some suitable agent in normally inhaled air, and it will often be the case that it is best to deliver the agent as a "spike" or short pulse at some selected point within the Patient's breathing cycle.

The present invention proposes treatment apparatus—specifically and in particular small (pocket-sized) hand-held apparatus—that utilises the "spike" principle. It suggests apparatus for the delivery of a medicament into the Patient's lungs in the form of a bolus, pulse, or spike of the medicament entrained in and driven by the normal respiration air, which apparatus comprises a drug dispenser (that in essence may be a conventional nebuliser or a dry-powder delivery system 11), in the reservoir (12) of which is stored the medicament to be administered, driven by some suitable pressurised gas from a valved cylinder (18) thereof to deliver an aerosol cloud of medicament into a tube (103) through which the Patient is breathing (by mouth) normal air, the gas cylinder valve (19) being controlled by a suitably programmed computing device (101) that is fed data describing the pressure within the breathing tube (103) and so is able to open and close the valve (19) at and for a time such as to drive the dispenser (11) to deliver (to the tube and thence to the Patient's lungs) a required pulse of medicament at any selected point within the Patient's respiratory cycle.

20 Claims, 2 Drawing Sheets

INHALERS

FIELD OF THE INVENTION

This invention relates to inhalers, and concerns in particular medical inhaler apparatus for use in the treatment of certain lung diseases or conditions.

BACKGROUND OF THE INVENTION

In the Specification of British Patent Application No: 2,283,179 (which corresponds to published PCT International Application WO 95/10,315) there is described and claimed a novel method, and associated apparatus, for the use of nitric oxide in the treatment of various lung conditions and diseases. The present invention relates to improved apparatus which can be used not only for this purpose but also in the treatment of other lung problems.

There are many lung diseases and conditions—suffered both by humans and by other animals—for which the preferred form of treatment involves delivering a medicament of the appropriate sort down the Patient's airways into the lungs themselves, where the medicament can act upon, and perhaps be absorbed into, the tissues of the lungs. One such condition is asthma (an increasingly prevalent and worrying problem), in which the peripheral parts of the lung, namely those tiny airways and air spaces known respectively as bronchioles and alveoli, constrict to restrict the flow of air therethrough.

In other lung conditions the lung's small peripheral arteries—the pulmonary arteries—also constrict, typically those deep in the lungs where the oxygen tension falls as in an asthmatic attack, pneumonia, or chronic lung diseases like bronchitis and emphysema (and it should also be noted that such constriction often occurs without the causative mechanism being fully explained; this is the so-called primary pulmonary hypertension).

The most effective treatments for asthma and like conditions involve the inhalation as an aerosol of some suitable chemical agent in normally inhaled air. At present, to deal with the problem of constricted small pulmonary arteries only a few relieving substances are known, and one of the most powerful—that known as prostacyclin, an extremely potent vasodilator—has to be administered on a continuous basis by infusion into a vein and so to the pulmonary arteries.

The aforementioned British and International Specifications relate to the use of nitric oxide (NO), another well-known and effective dilating agent for treating both lung problems of the blood-vessel-constriction type and of the asthma airway type. More specifically, these Specifications concern the manner in which nitric oxide is administered, and the apparatus used for this administration; they propose that the nitric oxide be administered to the Patient not continuously (either in admixture with, or separately but side by side with a supply of, air, oxygen or oxygen-enriched air) but intermittently and in short pulses of known, predetermined volume at one or more suitable time during each inhalation. In the treatment of the constriction of the small pulmonary arteries the very short pulse, or spike, of nitric oxide is provided at the start of the inhalation, such that the resultant bolus of nitric oxide mixture inhaled by the Patient has a nitric oxide concentration high enough to have the desired therapeutic effect, even if admixed with some additional air, but is of such short duration (both in time and, as a result, in physical length) that, pushed by the following much larger volume of plain, and therefore nitric oxide-free, air/oxygen, it reaches deeper into the lungs, where it both acts on the small pulmonary arteries and is taken up into the capillaries to react with haemoglobin (so preventing the formation of nitrogen dioxide). By contrast, in the treatment of asthma-like airway diseases or conditions the very short pulse of nitric oxide is timed to fall just before the end of the inhalation. This leaves the nitric oxide in contact with the airway smooth muscle in sufficient concentration to cause relaxation, but because at the end of the inhalation the airway is flushed of all the nitric oxide by the air coming from alveoli and lung periphery, so there is avoided prolonged exposure with the consequent risk of the formation of toxic nitrogen dioxide.

SUMMARY OF THE INVENTION

This previous invention concerns the administration of nitric oxide. The present invention stems from the appreciation that the same controlled breathing-related "pulsatile" delivery to the Patient's lungs can be usefully employed with many other medicaments; the invention is thus treatment apparatus—and in particular small (pocket-sized) hand-held apparatus—that utilises the "spike" principle. More specifically, the invention proposes apparatus for the delivery of a medicament—a drug, which can be in liquid or in solid (powder) form—into the Patient's lungs in the form of a bolus, pulse, or spike of the medicament entrained in and driven by the normal respiration air, which apparatus comprises in essence a drug dispenser (which might be a conventional liquid-dispensing nebuliser or a dry-powder dispenser, in the reservoir of which is stored the medicament to be administered), driven by some suitable pressurised gas from a completely separate valved cylinder thereof to deliver an aerosol cloud of medicament into a tube through which the Patient is breathing (by mouth) normal air, the gas cylinder valve being controlled by a suitably programmed computing device that is fed data describing the pressure within the breathing tube and so is able to open and close the valve at and for a time such as to drive the drug dispenser to deliver (to the tube and thence to the Patient's lungs) a required pulse of medicament at any selected point within the Patient's respiratory cycle. The provision of pulses of medicament is not in itself unknown, and one typical case is the asthma-treatment device the subject of Aradigm (Goodman et al) U.S. Pat. No. 5,404,871, which described an inhaler wherein a computer suitably controls the delivery of a medicament from a propellant-driven reservoir thereof. However, using a combination propellant/medicament source like that makes it quite difficult fully to control the manner in which the medicament is delivered to the Patient; the present invention deals in part with this by having the medicament reservoir and the driving gas source completely separate.

In one aspect, therefore, the invention provides miniature, pocket-sized, hand-holdable apparatus for the delivery of a medicament into the Patient's lungs in the form of a bolus, pulse, or spike of the medicament entrained in and driven by the normal respiration air, which apparatus comprises:

- a tube through which the Patient is able to breath (by mouth) normal air;
- a drug dispenser (in the reservoir of which is storable the medicament to be administered) the output of which is deliverable into the tube for inhalation by the Patient;
- separate from the dispenser, a valved cylinder for a suitable pressurised gas, which cylinder is operatively connectable to the dispenser so as in use to drive the dispenser to deliver an aerosol cloud of medicament into the tube;

pressure sensing means located within or operably connected to the tube, and able to provide data about the air pressure therewithin, and thus about the Patient's respiratory cycle; and programmed computing means operatively connectable to the gas cylinder valve so as to be able to open and shut that valve, and able to receive pressure data from the pressure sensing means;

such that the computing means can utilise the pressure data to enable the gas cylinder to drive the dispenser to deliver (to the tube and thence to the Patient's lungs) a required pulse of medicament at any selected point within the Patient's respiratory cycle.

The apparatus of this invention is intended to be portable. Indeed, it is the primary purpose of the invention to provide the apparatus in light, pocket-sized form small enough to be held in the hand, and to be used while being so held, and accordingly, hereinafter the apparatus is described in terms most appropriate for such a small hand-held piece of kit.

The invention provides apparatus for the delivery of a medicament into the Patient's lungs. The medicament can be any such material that might need to be administered to the lungs. For example, to treat asthma the medicament could be a bronchodilator such as SALBUTAMOL or TERBUTALINE or a steroid such as BECLOMETHASONE or FLIXOTIDE, while to treat an actual lung infection the medicament might be an antibiotic such as TICARCILLIN or COLISTIN.

The medicament may be formulated in any way that is both appropriate to the active ingredient of the medicament and to the need to have it turn into an aerosol spray in use. It may be presented as a solution or suspension in some liquid—water, perhaps—or it may even be supplied as a fine powder, possibly with or absorbed onto a powder carrier (when in a liquid form the drug is delivered to the Patient as an aerosol of fine droplets; when in solid/powder form it is delivered as a cloud of dust particles). By way of example, the asthma-treating medicament FLIXOTIDE is conveniently used in the form of dry powder, while the sputum lytic agent rhDNAse is advantageously delivered in the form of a liquid aerosol (droplets of liquid suspended in gas).

The invention's apparatus delivers its medicament into the lungs in the form of a bolus, pulse, or spike of the medicament entrained in and driven by the normal respiration air. The idea of this is simply to ensure that a high proportion of the medicament reaches and affects the target area and the target area only, rather than having the whole of the lungs subjected to it. The smaller the bolus—the shorter the pulse—the better this specificity is achieved. In some cases the pulse will be very short indeed, and while it is difficult to define precisely what is meant by "very" short, the following comments may be of assistance. The term "very short" means primarily that the provision of sufficient medicament for each bolus thereof is achieved by supplying the driving gas for a time period—of the order of a few tens of milliseconds—that is very short compared with the length of an average inhalation (which is about 1.5 second). However, there is more to the shortness of the pulse than just its temporal duration, for, the purpose of the pulse being to provide a bolus of medicament both of relatively high concentration and of relatively short physical length, both the actual flow rate of the medicament (perhaps in its carrier mixture form) as it is fed to the Patient and also the actual concentration of the medicament in that fed gas are important factors. What has been determined by experiment is that very satisfactory results are obtained using pulse durations of a few tens of milliseconds, and typically 20 to 30 msec.

Thus, while it will clearly be understood that what is a "very short" pulse depends upon the flow rate and concentration of the administered medicament, nevertheless it can now be said that the term "very short" means "of the order of a few units or tens of milliseconds". Or, to put it another way, the term means roughly one thousandth of the length of an average inhalation.

In the apparatus of the invention the medicament is driven into the Patient's lungs through a tube through which the Patient is breathing (by mouth) normal air. This tube is essentially nothing more than a short open-ended hollow cylinder—say, 5 in (13 cm) long and 1 in (2.5 cm) external diameter—possibly with a flattened mouthpiece to make it more convenient for the Patient to use, and nothing more need be said about it here.

The apparatus of the invention incorporates a drug dispenser in the reservoir of which is storable the medicament to be administered. It is the output of the dispenser which is deliverable into the tube for inhalation by the Patient.

One form of drug dispenser is the conventional nebuliser. Nebulisers—"cloud-formers"—are in general well-known items of equipment, commonly encountered in scent sprays, aerosol sprays, and carburettors, and little need be said about them here. Even so, it is convenient to note that a nebuliser is a basically a reservoir that has a fine orifice through which its contents may exit and across which is blown a stream of gas along a pipeway. As the gas flows past the orifice it causes an external pressure drop (relative to the reservoir's internal pressure: this pressure drop can be enhanced by shaping the pipeway as a Venturi constriction at the appropriate position), and so some of the reservoir's contents is "sucked" out into the gas stream and breaks up into an aerosol-like cloud of drops or particles that is then swept along the pipeway by the:driving gas. It is convenient to include within the pipeway downstream of the orifice an obstacle, or baffle, that is positioned within the path of the emerging drop/particle stream so as to impede all but the smallest drops/particles, which smallest ones are of a size most appropriate to being transported to the farthest reaches of the lung. For a small hand-held device the nebuliser is conveniently around 2.5 in (6 cm) long and an inch (2.5 cm) or so across, the reservoir holding perhaps 1.5 cu. in (25 cc) of medicament formulation.

An alternative form of dispenser is the dry-powder dispenser, another well-established piece of equipment in which fine particles of medicament are held without liquid (indeed in some cases are created at the time of use by abrasion of a solid or compacted tablet) and are caused to enter the inspired airstream.

The drug dispenser (of whatever sort) employed in the invention's apparatus is driven by a suitable gas from a valved cylinder thereof, so as to produce the desired aerosol cloud of medicament and drive it into the tube. This gas can be simply a carrier—thus, an effectively inert (to the Patient) gas such as carbon dioxide or nitrogen—but it may be advantageous if the gas itself have some suitable medicinal action. For example, the gas might well be nitrous oxide ($N_2O$). There is little else to say about this, save that gas in the cylinder is likely to be at a high pressure, and so should be regulated to provide a lower, and constant, pressure appropriate to the operation of the dispenser, and save also that the gas cylinder (and any regulating means) should clearly be of a size and strength suitable to its intended purpose—and for a hand-held device an appropriate size is, much like the drug dispenser, around 3 in (7.5 cm) long and an inch (2.5 cm) or so across, and holding perhaps 2 cu. in (35 cc) of liquified gas under a pressure of 50 bar (3 MPa, or 700 lbs/sq. in).

The cylinder is, of course, a valved cylinder, and the operation of the valve is controlled by the computing means (via some suitable actuating means) in response to the computing means' programming and input from the pressure sensor. The valve mechanism may take any appropriate form—it is typically an electromagnetically-actuated device such as one of those miniature solenoid valves available from Parker Hannifin Corp., Pneutronics Div., Hollis, N.H., USA, and is conveniently powered from the computing means' power source.

The invention's apparatus includes pressure sensing means located within or connectable to the tube, and in use providing the computing means with data about the air pressure therewithin, and thus about the Patient's respiratory cycle. The sensor may be any suitable pressure-detecting transducer with an electrical output, and one preferred sensor is that available under the designation 24/26 PC from Honeywell Inc., Freeport, Ill., USA.

Controlling the whole operation of the medicament administering apparatus of the invention is the programmed computing means. This is operatively connectable to the gas cylinder valve (via its actuating means) so as to be able to open and shut that valve, it receives pressure data from the pressure sensing means so that it "knows" at all times the progress of the Patient's respiratory cycle, and it is programmed to make use of that information so as to enable the gas cylinder to drive the drug dispenser to deliver (to the tube and thence to the Patient's lungs) a required pulse of medicament at any selected point within that cycle. Notionally, the computing means could be a general purpose microcomputer appropriately programmed and able to deal with the relevant inputs and outputs from and to the real world. In practice, though, the computing means is most advantageously a simple single chip computer "hard wired", or programmed in ROM, to take the relevant actions. Such a computer can be no more than 2 in (5 cm) or so long and wide, and 0.5 in (1.25 cm) deep, and can run off a small battery. It is ideally suited for use in a hand-held medicament-delivery system.

The programmed computing means takes the pressure data and in accordance with its program makes use of that information so as to enable the gas cylinder to drive the drug dispenser to deliver (to the tube and thence to the Patient's lungs) a required pulse of medicament at any selected point within that cycle. Which point that is, and for how long the pulse will last, is dependent upon the Patient's illness and the medicament being taken (this has been touched upon hereinbefore). The treatment of some conditions might require very short pulses to be delivered right at the beginning of the inspiration phase of the respiratory cycle—as the Patient draws in the next breath—while in contrast the treatment of others might require rather longer pulses to be delivered at the end of the inspiration phase of the respiratory cycle—as the Patient finishes inhaling the present breath and just before the exhale starts.

The primary purpose of the programmed computing means is to control the dispensing of the relevant medicament in dependence upon the respiratory data it receives, and in this connection the operation of the dispenser may be improved if the computing means utilises an algorithm to optimize the detection of the breathing cycle in the presence of artefacts. In addition, however, the computing means can usefully gather data about the patient's respiration, and about apparatus usage and drug-dispenser changes, and then compute (and present) details of the patient's respiratory statistics, and so on. Moreover, it may be desirable to provide additional control of apparatus usage in accordance with data that may be pre-programmed into the apparatus or even encoded on (and read off) the drug container, or computed from the detected patient breathing cycle. Additionally, it may be desirable to enable the prevention of drug delivery in the absence of appropriate User/Patient identification by means of button/keyboard interaction. Accordingly, preferred embodiments of the medicament delivery apparatus of the invention include the following:

- A coding system (whether optical, electrical or by physical shape or other means) by which the contents of the drug container and the date limits of its contents may be detected by the programmed computing means and. reported to the user, or employed in the control of the drug-dispensing process.
- A visual or audible display system in which information may be provided to the User on the operation of the device, the status of the drug container or the parameters of their breathing process as measured by the. pressure-sensing means and computed by the programmed computing means.
- A means whereby the User may provide information to the programmed computing means, typically one or more electrical buttons or a miniature keypad.

BRIEF DESCRIPTION OF THE DRAWINGS

An embodiment of the invention is now described, though by way of illustration only, with reference to the accompanying Drawings in which.

DETAILED DESCRIPTION OF THE INVENTION

Figure 1:
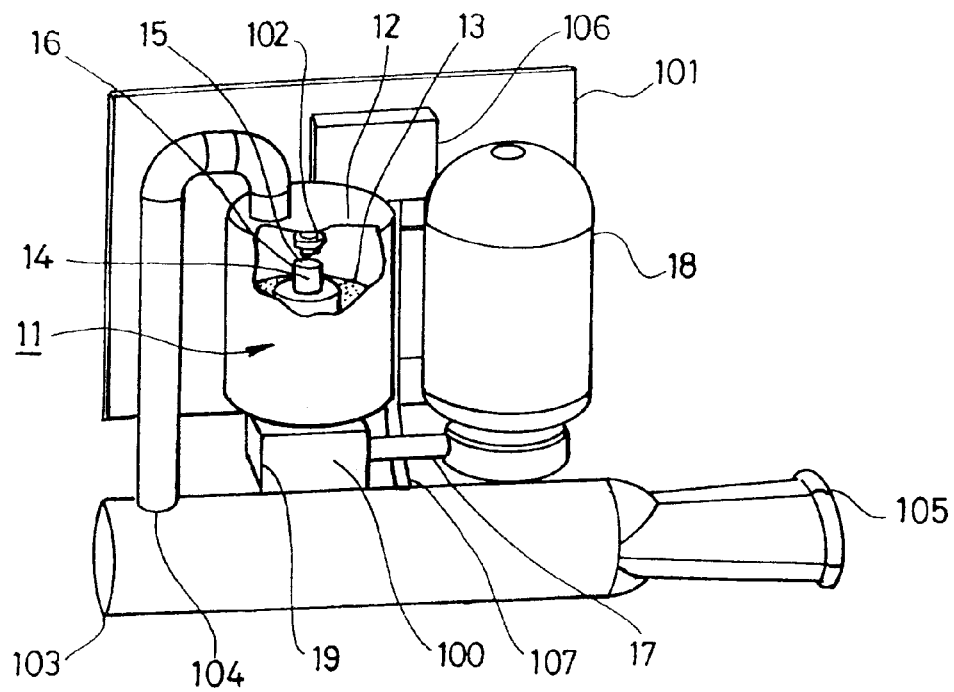
FIG. 1 shows in cut-away perspective form apparatus of the invention for administering a medicament in controlled pulses to the Patient's lungs.

The apparatus shown in FIG. 1 is in principle very simple. It comprises a drug dispenser in the form of a nebuliser (generally 11) having a reservoir (12) of medicament formulation (13) having an output tube (14) open as a "jet" (15) at the top (as viewed) to the "outside". The jet orifice is within a Venturi portion (16) of a deliver pipe (17) along which is fed pressurised gas from a storage cylinder (18) via a control valve (19). The valve is operated by actuating means (100) itself driven by control signals from a single chip microcomputer (101: shown as a flat board).

The released gas and the "sucked out" medicament pass, via a baffle (102), into the apparatus' main breathing tube (103) by way of a second jet orifice (104), and there it mixes with the air that the Patient (not shown) draws in through a mouthpiece (105) at the tube's open end to provide lung-filling breaths.

A pressure-sensing transducer (106) is connected by a short pipe (107) opening into the tube 103 roughly intermediate the two ends. The transducer's output is fed to the microcomputer 101. The microcomputer uses this information to enable the gas cylinder valve 19 at predetermined times and for a predetermined duration in accordance with its programming (which is tailored to fit the Patient's disease or condition).

Figure 2:
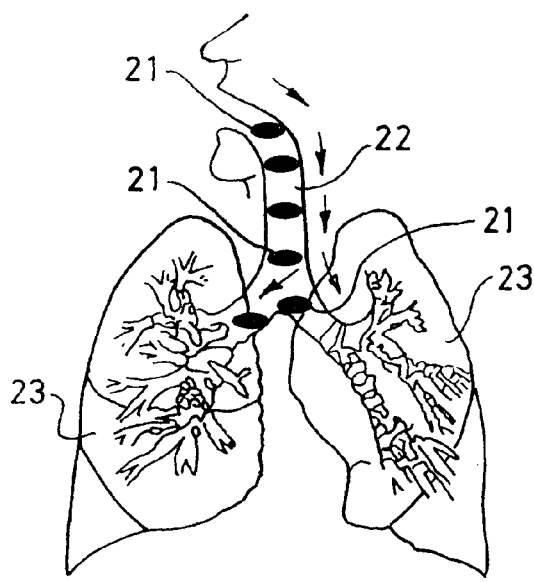
FIG. 2 shows a bolus of medicament/air mixture travelling down deep into the Patient's lungs.

FIG. 2 shows the progress of a bolus (21) of medicament/air mixture down the Patient's windpipe (22) and on deep into his lungs (23). Though at first sight it looks as though there are several bolus preceding one after the other, in fact there is only one, shown at different times on its journey, and the object of the Figure is to show how the bolus remains as an entity, and does not disperse as it progresses (and so reaches the deepest part of the lungs as a concentrated burst of medicament with the full therapeutic effect required).

Figure 3:
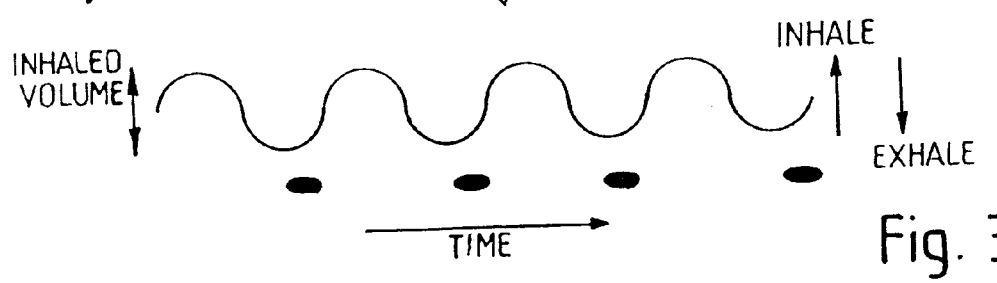
FIG. 3 shows graphically the Patient's respiration, and the timing of the medicament pulses at the start of an inhalation.
Figure 4:
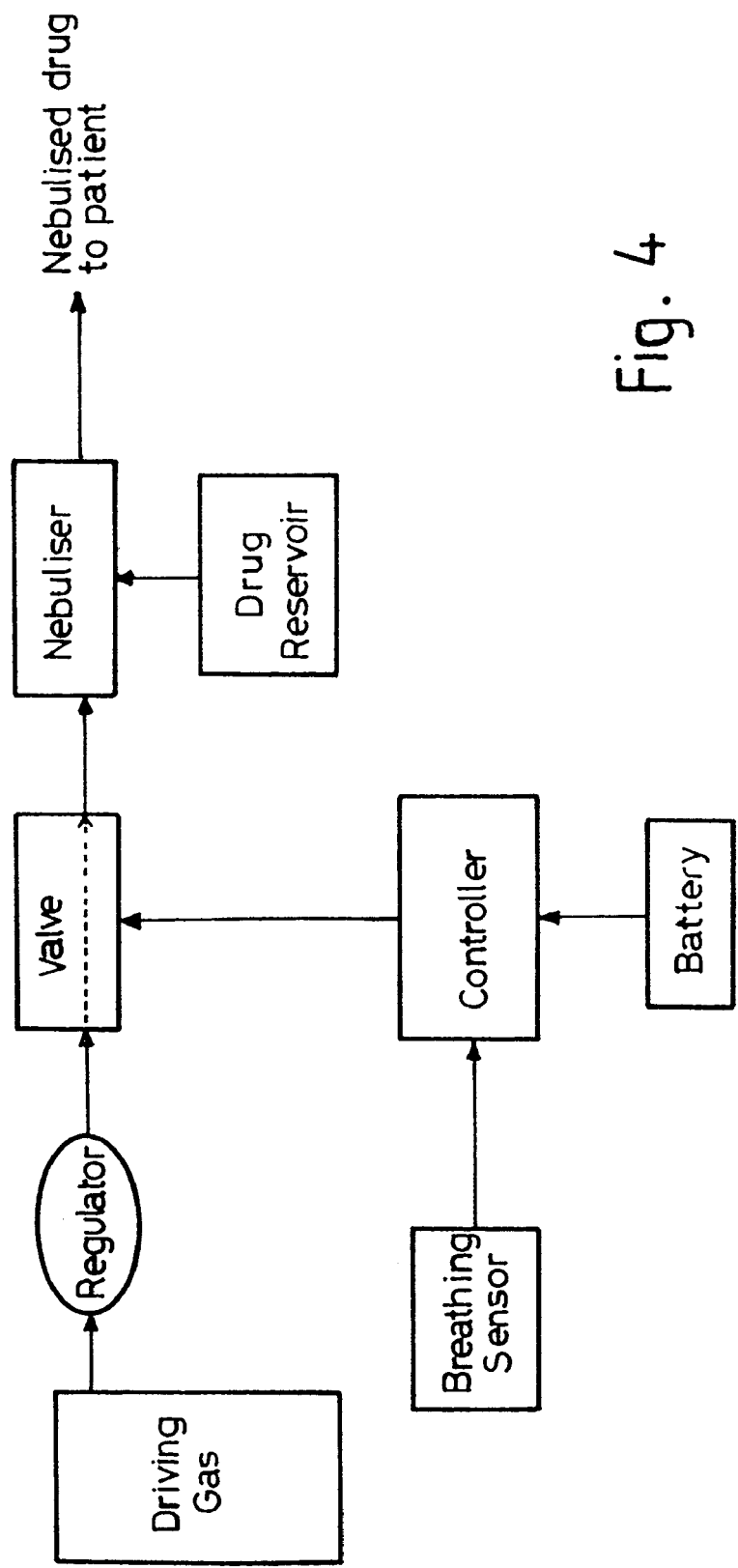
FIG. 4 is a black box schematic of the overall drug dispenser/microcomputer system of the invention.

The timing of the bolus delivery is shown graphically in FIG. 3. Airflow in and out of the lungs takes place at regular intervals, as the Patient breathes, and just as the flow starts a pulse of medicament is delivered, and "washed down" with the remaining inhaled air.

The black box schematic of FIG. 4 indicates the manner in which the microcomputer 101 operates in connection with the other parts.

What is claimed is:

1. A pocket-sized, hand-holdable apparatus for the delivery of a medicament into a Patient's lungs in the form of a bolus, pulse or spike of the medicament entrained in and driven by the normal respiration air, comprising:

a tube through which the Patient is able to breath normal air;

a reservoir;

a drug dispenser in the reservoir of which is storable the medicament and having an output coupled to deliver the medicament into the tube for inhalation by the Patient; and a pressure sensor operably connected to the tube, and able to provide data about the air pressure therewithin, and thus about the Patient's respiratory cycle;

separate from the dispenser, a valved cylinder for a pressurised gas, which cylinder is connectable to the dispenser so as to drive the dispenser to deliver an aerosol cloud of medicament into the tube; and programmed computing means operatively connectable to the gas cylinder valve so as to be able to open and shut that valve, and able to receive pressure data from the pressure sensor;

such that the computing means can utilise the pressure data to enable the gas cylinder to drive the dispenser to deliver to the tube and thence to the Patient's lungs, a pulse of medicament at any selected point within the Patient's respiratory cycle.

2. Apparatus as claimed in claim 1, wherein the tube is a short, open-ended, hollow cylinder with a flattened mouthpiece.

3. Apparatus according to claim 1 wherein the drug dispenser is a nebuliser that has an orifice through which the medicament in the reservoir may exit, and wherein the valved cylinder is connectable to the dispenser via a pipeway so as to blow a stream of gas along the pipeway that picks up the contents of the reservoir, and the pipeway including, downstream of the orifice, a baffle positioned so as to impede the stream of gas and medicament.

4. Apparatus according to claim 3 further including a regulator disposed between the valved cylinder and the drug dispenser to provide a lower, constant pressure along the pipeway.

5. Apparatus according to claim 4 wherein the valved cylinder comprises an electromagnetically-actuated solenoid valve.

6. Apparatus according to claim 5 wherein the pressure sensor is spaced from but connectable to the tube.

7. Apparatus according to claim 4 wherein the pressure sensor is spaced from but connectable to the tube.

8. Apparatus according to claim 3 wherein the valved cylinder comprises an electromagnetically-actuated solenoid valve.

9. Apparatus according to claim 8 wherein the pressure sensor is spaced from but connectable to the tube.

10. Apparatus according to claim 3 wherein the pressure sensor is spaced from but connectable to the tube.

11. Apparatus according to claims 3 wherein the pressure sensor is or includes a pressure-detecting transducer with an electrical output.

12. Apparatus according to claim 1 further including a regulator disposed between the valved cylinder and the drug dispenser to provide a lower, and constant pressure along the pipeway.

13. Apparatus according to claim 12 wherein the valved cylinder comprises an electromagnetically-actuated solenoid valve.

14. Apparatus according to claim 14 wherein the pressure sensor is spaced from but connectable to the tube.

15. Apparatus according to claim 12 wherein the pressure sensor is spaced from but connectable to the tube.

16. Apparatus according to claim 1 wherein the valved cylinder comprises an electromagnetically-actuated solenoid valve.

17. Apparatus according to claim 16 wherein the pressure sensor is spaced from but connectable to the tube.

18. Apparatus according to claim 1 wherein the pressure sensor is spaced from but connectable to the tube.

19. Apparatus according to claim 1 wherein the pressure sensor is or includes a pressure-detecting transducer with an electrical output.

20. Apparatus according to claim 1 wherein the programmed-computing means is a chip computer.

* * * * *